United States Patent
Pederson

(10) Patent No.: US 9,844,667 B2
(45) Date of Patent: Dec. 19, 2017

(54) SYSTEM FOR CONDITIONING SURFACES IN VIVO

(75) Inventor: Brian D. Pederson, Plymouth, MN (US)

(73) Assignee: Medtronic ATS Medical Inc., Minneapolis, MN (US)

( * ) Notice: Subject to any disclaimer, the term of this patent is extended or adjusted under 35 U.S.C. 154(b) by 2941 days.

(21) Appl. No.: 11/402,463

(22) Filed: Apr. 12, 2006

(65) Prior Publication Data

US 2007/0244536 A1    Oct. 18, 2007

(51) Int. Cl.
*A61N 1/20* (2006.01)

(52) U.S. Cl.
CPC ..................... *A61N 1/20* (2013.01)

(58) Field of Classification Search
CPC ....................................................... A61N 1/20
USPC ..... 607/2, 50, 63, 72, 75, 76, 115, 116, 121; 623/2.1
See application file for complete search history.

(56) References Cited

U.S. PATENT DOCUMENTS

| | | | |
|---|---|---|---|
| 3,609,768 A | 10/1971 | Ayres et al. | |
| 3,757,794 A | 9/1973 | Cannon et al. | |
| 4,038,702 A | 8/1977 | Sawyer | |
| 4,945,912 A | 8/1990 | Langberg | |
| 4,979,955 A * | 12/1990 | Smith | 623/2.2 |
| 5,078,763 A | 1/1992 | Blount-Gillette | |
| 5,197,980 A * | 3/1993 | Gorshkov et al. | 623/2.1 |
| 5,348,553 A | 9/1994 | Whitney | |
| 5,464,438 A | 11/1995 | Menaker | |
| 5,603,731 A * | 2/1997 | Whitney | 607/121 |
| 5,741,852 A | 4/1998 | Marchant et al. | |
| 5,895,419 A | 4/1999 | Tweden et al. | |
| 5,924,975 A | 7/1999 | Goldowsky | |
| 5,993,890 A | 11/1999 | Marchant et al. | |
| 6,047,700 A | 4/2000 | Eggers et al. | |
| 6,110,204 A | 8/2000 | Lazarov et al. | |
| 6,206,914 B1 | 3/2001 | Soykan | |
| 6,560,489 B2 * | 5/2003 | Hauck | 607/62 |
| 6,632,215 B1 | 10/2003 | Lemelson | |
| 6,658,288 B1 | 12/2003 | Hayashi | |
| 2001/0000802 A1 | 5/2001 | Soykan et al. | |

(Continued)

FOREIGN PATENT DOCUMENTS

| | | |
|---|---|---|
| EP | 0 643 601 A1 | 1/2001 |
| SE | 1 566 472 | 4/1980 |

(Continued)

OTHER PUBLICATIONS

Golomb, "Prevention of Bioprosthetic Heart Valve Tissue Calcification by Charge Modification: Effects of Portamine Binding by Formaldehyde", Journal of Biomedical Materials Research, 1991, vol. 25, No. 1, pp. 85-98.

(Continued)

*Primary Examiner* — Christopher D Koharski
*Assistant Examiner* — Roland Dinga

(57) ABSTRACT

A system and method for conditioning surfaces of a body in vivo includes providing an electrical energy source, coupling the electric energy source to the surface, and delivering electropositive current from the electrical energy source to the surface so as to generate a sub-threshold current density on the surface. In preferred embodiments, the sub-threshold electropositive current density is between about 0.001 and about 1.0 mA/cm$^2$.

32 Claims, 4 Drawing Sheets

(56) References Cited

U.S. PATENT DOCUMENTS

| | | | |
|---|---|---|---|
| 2002/0120297 A1 | 8/2002 | Shadduck | |
| 2003/0078624 A1* | 4/2003 | Carlson et al. | 607/9 |
| 2003/0229376 A1 | 12/2003 | Sandhu | |
| 2004/0039417 A1* | 2/2004 | Soykan et al. | 607/2 |
| 2004/0215310 A1 | 10/2004 | Amirana | |
| 2005/0021134 A1* | 1/2005 | Opie | 623/2.2 |
| 2005/0143802 A1 | 6/2005 | Soykan et al. | |
| 2006/0009804 A1 | 1/2006 | Pederson | |

FOREIGN PATENT DOCUMENTS

| | | |
|---|---|---|
| WO | WO 88/01155 | 2/1988 |
| WO | WO 93/25273 | 12/1993 |
| WO | WO 94/11411 | 5/1994 |
| WO | WO 94/25081 | 11/1994 |
| WO | WO 95/19796 | 7/1995 |
| WO | WO 99/36193 | 7/1999 |
| WO | WO 99/44519 | 9/1999 |
| WO | WO 03/037400 | 5/2003 |
| WO | WO 2005/004754 | 1/2005 |

OTHER PUBLICATIONS

Speer et al., "Regulation of Cardiovascular Calcification", Cardiovascular Pathology, 2004, vol. 13, No. 2 (Mar-Apr), pp. 63-70.

Shih et al., "Characterization of the Thrombogenic Potential of Surface Oxides on Stainless Steel for Implant Purposes", Applied Surface Science, vol. 219, No. 3-4, pp. 347-362, Dec. 15, 2003.

Nazli et al., "Diagnostic Value of D-Dimer and Antithrombin-III Levels in Predicting Prosthetic Heart Valve Thrombosis", Cardiovasc. Surg., Isparta, Turkey, Texas Heart Insitute Journal, 2003, vol. 30, No. 4, pp. 268-279.

Butany et al., "Prosthetic Heart Valves with Silver-Coated Sewing Cuff Fabric: Early Morphological Features in Two Patients", Canadian Journal of Cardiology, 2002, vol. 18, No. 7 (Jul), pp. 733-738.

Sawyer et al., "Electrochemistry of Thrombosis. An Aid in the Selection of Prosthetic Materials", Journal of Biomedical Materials Research, vol. 4, No. 1 (Mar. 1970), pp. 43-55, 1970.

* cited by examiner

SYSTEM FOR CONDITIONING SURFACES IN VIVO

FIELD OF THE INVENTION

The present invention relates to systems and methods for conditioning various surfaces in vivo generally, and more particularly to systems and methods for inhibiting blood platelet adhesion on such surfaces, and specifically blood platelet adhesion to surfaces of implanted medical devices.

BACKGROUND OF THE INVENTION

Many surfaces in the human body that are exposed to blood flow are at risk of blood component deposit formation thereon. Such deposits can include, for example, blood platelets, fibrinogen, minerals such as calcium, and the like. Deposit formation on surfaces located at areas of the body which are critical to blood transmission can be detrimental or even hazardous to the person's health. For example, deposit formation on heart valves, veins, and arteries can restrict the flow of blood therethrough and/or reduce the functionality thereof. As a result, deposit formation can lead to obstructed blood flow through at least portions of the body, which limited blood flow can have serious negative implications on the health of the person.

A common form of coagulative deposition on surfaces within the body is thrombosis. This phenomenon is a result of cumulative blood component adhesion to a surface, and can have a variety of causes. In some cases, thrombosis is believed to be caused by turbulence in the blood stream, with such turbulence causing relatively forceful impact among red blood cells that causes damage to the cells, and ultimately proneness to adhere to surfaces.

While thrombosis can and does occur around native tissue surfaces, it has been found that implanted medical devices often times act as focal points for thrombogenesis. Virtually all types of implanted medical devices bear some thrombogenic characteristics, in that the implantation of such devices typically alter to some extent the normal interaction of blood flow at the implantation site. Some medical devices, however, have been found to be particularly susceptible to thrombogenesis. Artificial heart valves are an example of such implanted medical devices that bear relatively significant thrombogenetic characteristics. While materials and design for recently developed heart valves have reduced the risk of thrombogenesis, patients receiving such artificial heart valves typically are required to maintain an anticoagulative drug protocol for the remainder of their lives. Current anti-coagulative drug therapy is far from ideal. Each patient with an implanted heart valve not only carries a risk for valve thrombosis or systemic emboli, but also a risk of bleeding which follows anti-coagulant therapy. Thromboemboli and hemorrhage comprise the majority of complications occurring in patients with artificial heart valves.

It is therefore a principal object of the present invention to provide a method for inhibiting thrombogenesis on a surface of a body in vivo with a reduced or eliminated need for anti-coagulant medication.

It is a further object of the present invention to provide a method for inhibiting thrombogenesis on the surface of a body in vivo by delivering electropositive current to such surface.

It is a still further object of the present invention to provide a method for inhibiting blood component coagulation on a surface of an implanted medical device by delivering sub-threshold electropositive current from an electrical energy source to the surface of the implanted medical device.

It is a still further object of the present invention to inhibit blood platelet adhesion to a surface in vivo by coupling the surface to an implanted electrical energy source, wherein such electrical energy source provides an electropositive current density on the surface of between about 0.001 and about 1 $mA/cm^2$ to the target surface.

SUMMARY OF THE INVENTION

By means of the present invention, thrombogenesis on one or more surfaces of a body in vivo may be substantially inhibited without the aid of anticoagulant medication. Applicant has discovered that blood platelet adhesion to surfaces in vivo can be thwarted by applying a sub-threshold electropositive current to such surfaces. A preferred range of electropositive current density applied to target surfaces in vivo is between about 0.001 and about 1 $mA/cm^2$.

In a particular embodiment, a method for inhibiting thrombogenesis on a surface of a body in vivo includes providing an electrical energy source, coupling the electrical energy source to the surface, and delivering electropositive current from the electrical energy source to the surface so as to generate an electropositive current density of between about 0.001 and about 1 $mA/cm^2$ on the surface.

In preferred embodiments, the surface is electrically conductive, and in some cases is a portion of an implanted medical device.

In another embodiment, a method for inhibiting blood platelet adhesion to a surface in vivo includes applying electrical energy to the surface, with the electrical energy being derived from an electropositive current providing an electropositive current density of between about 0.001 and about 1 $mA/cm^2$ on the surface.

A system for inhibiting thrombogenesis on a surface in vivo includes an electrical energy source that is electrically coupled to the surface, with the electrical energy source providing electropositive current density of between about 0.001 and about 1 $mA/cm^2$ on the surface.

DETAILED DESCRIPTION OF THE PREFERRED EMBODIMENTS

The objects and advantages enumerated above together with other objects, features, and advances represented by the present invention will now be presented in terms of detailed embodiments described with reference to the attached drawing figures which are intended to be representative of various possible configurations of the invention. Other embodiments and aspects of the invention are recognized as being within the grasp of those having ordinary skill in the art.

Figure 1:
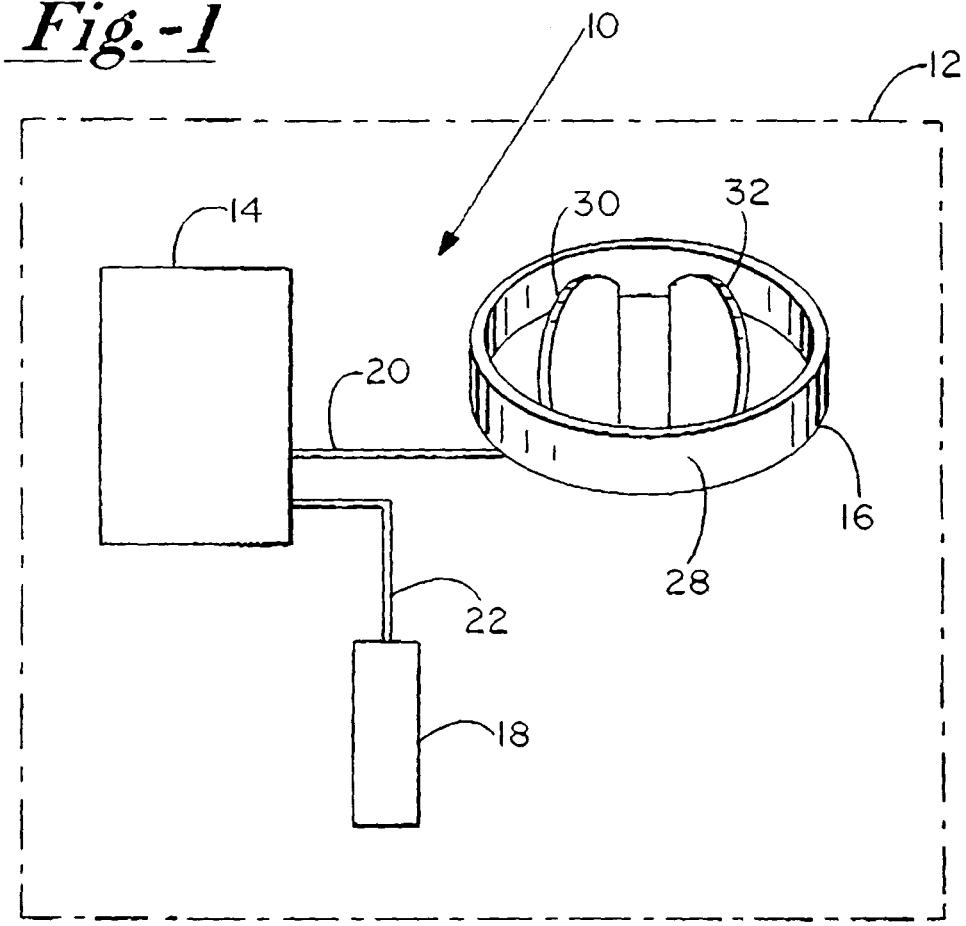
FIG. 1 is a schematic diagram of a surface conditioning system of the present invention.

With reference now to the drawing figures, and first to FIG. 1, a system 10 of the present invention is preferably disposed in the human body, which location is identified by area 12. Although the components of system 10 are illustrated in FIG. 1 as being in close proximity to one another, it is contemplated that such components may be disposed in a distributed fashion in the body. Due to the electrically coupled nature of the components of system 10, however, it is likely that most embodiments of the invention involve component proximity that is sufficiently close to enable electrical coupling through conventional means.

In the embodiment illustrated in FIG. 1, system 10 includes an electrical energy source 14, a medical device 16, and a return electrode 18. In some embodiments of the invention, return electrode 18 is incorporated into the structure of electrical energy source 14, such that a separate electrode element 18 is not required. In preferred embodiments, electrical energy source 14 is electrically coupled to medical device 16 through wire 20, and electrically coupled to electrode 18 through wire 22. Other conventional mechanisms for electrically coupling the components of system 10, however, are contemplated as being useful in the present invention. Depending upon the application, wire 20 may be connected to medical device 16 in general, or may instead be connected to medical device 16 at a specific location thereof, with the distinction being which portion of medical device 16 is targeted for receiving electrical current from electrical energy source 14. In many embodiments, it is desired to deliver electrical current to medical device 16 in its entirety. In some embodiments, however, it is desired that less than the entirety of medical device 16 receive electrical current from electrical energy source 14. Such distinctions direct the location of where current should be allowed to travel in medical device 16 from the wire connection point.

In an important aspect of the present invention, electrical energy source 14 preferably delivers electropositive current to medical device 16 through an electrical coupling, such as electrically conductive wire 20. The electropositive-biased current delivered to medical device 16 preferably generates a sub-threshold current density on medical device 16, in that the current density is below a threshold level required to stimulate adjacent tissue. Such a characteristic is particularly important in applications wherein medical device 16 is disposed at or adjacent to cardiac tissue. Incidental excitation of cardiac tissue through an applied electrical current could result in undesired contraction of cardiac tissue, and, correspondingly, impaired cardiac functionality. Typically, threshold electrical current density for cardiac tissue is about 75 mA/cm$^2$. As such, system 10 of the present invention preferably generates no more than 1 mA/cm$^2$ current density adjacent to cardiac tissue, so as to avoid undesired tissue excitation. Such a threshold level is also preferably utilized by system 10 of the present invention in non-cardiac applications, such that tissue adjacent to system 10 is not inadvertently excited.

In preferred embodiments, electrical energy source 14 delivers an electropositive current to create an electropositive current density of between about 0.001 and about 1 mA/cm$^2$ on the target surface. Such a current density range, however, may be broadened to other sub-threshold current densities, as required per application. In such cases, electropositive current density of somewhat greater than 1 mA/cm$^2$ may be required for optimal blood platelet adhesion-inhibiting results. Applicant has determined, however, that an electropositive current density of between about 0.001 and about 1 mA/cm$^2$ provides desirable levels of blood platelet adhesion inhibition on target surfaces.

The arrangement of system 10 illustrated in FIG. 1 provides for electropositive current delivery to medical device 16, due to the fact that electrode 18 acts as a "return" electrode to electrical energy source 14. Although the electropositive current may be delivered to medical device 16 through a variety of modalities, a particularly preferred mode of current transmission is in pulsatile format, wherein the pulsatile current is in one of a variety waveforms. Such waveforms may be, for example, sinusoidal, square, and triangular.

Electrical energy source 14 is preferably any device that is capable of producing and emitting electrical current from a designated location. Although electrical energy source 14 is illustrated in FIG. 1 as being implanted within body area 12, it is contemplated by the present invention that electrical energy source 14 may instead be placed extra-corporal while maintaining electrical coupling to a target surface, such as a surface of medical device 16. In some embodiments of the present invention, electrical energy source 14 is a commonly implanted electrical impulse device, such as a pacemaker or defibrillator. Conventional pacemaker devices either include, or may be modified to include, electrical leads to which wires 20, 22 may be connected. In some embodiments, such pacemaker-type devices include internal "return" electrodes that negate the necessity of including a separate electrode 18 in system 10. The arrangement illustrated in FIG. 1, however, does in fact utilize such an electrode 18, which electrode may be fabricated from, for example, titanium, and is preferably disposed subcutaneously in the body.

While system 10 has been described above with reference to the embodiment illustrated in FIG. 1, a number of other applications for the electropositive current generated by electrical energy source 14 are contemplated by the present invention. In particular, the application of sub-threshold electropositive current to a variety of surfaces is believed to be effective in inhibiting thrombogenesis thereon. Such surfaces, therefore, may include both native and non-native tissue, as well as implanted medical devices. For example, electrical energy source 14 may be electrically coupled to a native or non-native tissue heart valve for inhibiting blood platelet adhesion thereto. Other native or non-native tissue may also be conditioned through the system and method of the present invention. Such tissues include, for example, arterial walls, cardiac tissue, and the like. In other embodiments, electrical energy source 14 may be electrically coupled to an implanted medical device, such as medical device 16. A wide variety of implanted medical devices may be conditioned through the method and system of the present invention. Example implanted medical devices include mechanical heart valves, stents, guide wires, implanted drug delivery ports, and the like.

A particular aspect of the present invention is in the selective application of electropositive current to target surfaces. Such target surfaces may comprise any portion of a structure upon which the target surface resides. As such, the target surface that receives the electropositive current may involve the entire structure, or alternatively, less than the entire structure. In the embodiments illustrated in FIG. 1, medical device 16 may be wholly electrically conductive, such that electrical current delivered to can 28 of device 16 propagates to remaining elements thereof, such as valve leaflets 30, 32 thereof. In other embodiments, however, it may be desired that only valve leaflets 30, 32 of medical device 16 receive electropositive current, such that wire 20 is connected to a position of medical device 16 that is in electrical continuity with, for example, valve leaflets 30, 32, but electrically insulated from, for example, can 28. In preferred embodiments, therefore, the target surface to which electrical energy source 14 is electrically coupled is electrically conductive, so as to most efficiently transmit the electropositive current thereacross. The efficient transmission of electrical current throughout the target surface effectuates a high level of conditioning/treatment in inhibiting thrombogenesis thereon.

The following examples set forth specific conditions under which beneficial results of the system and method of the present invention have been observed. The examples provided hereinbelow, however, should not be construed to limit the scope of the invention to the specific operating conditions set forth therein.

Control

Figure 2:
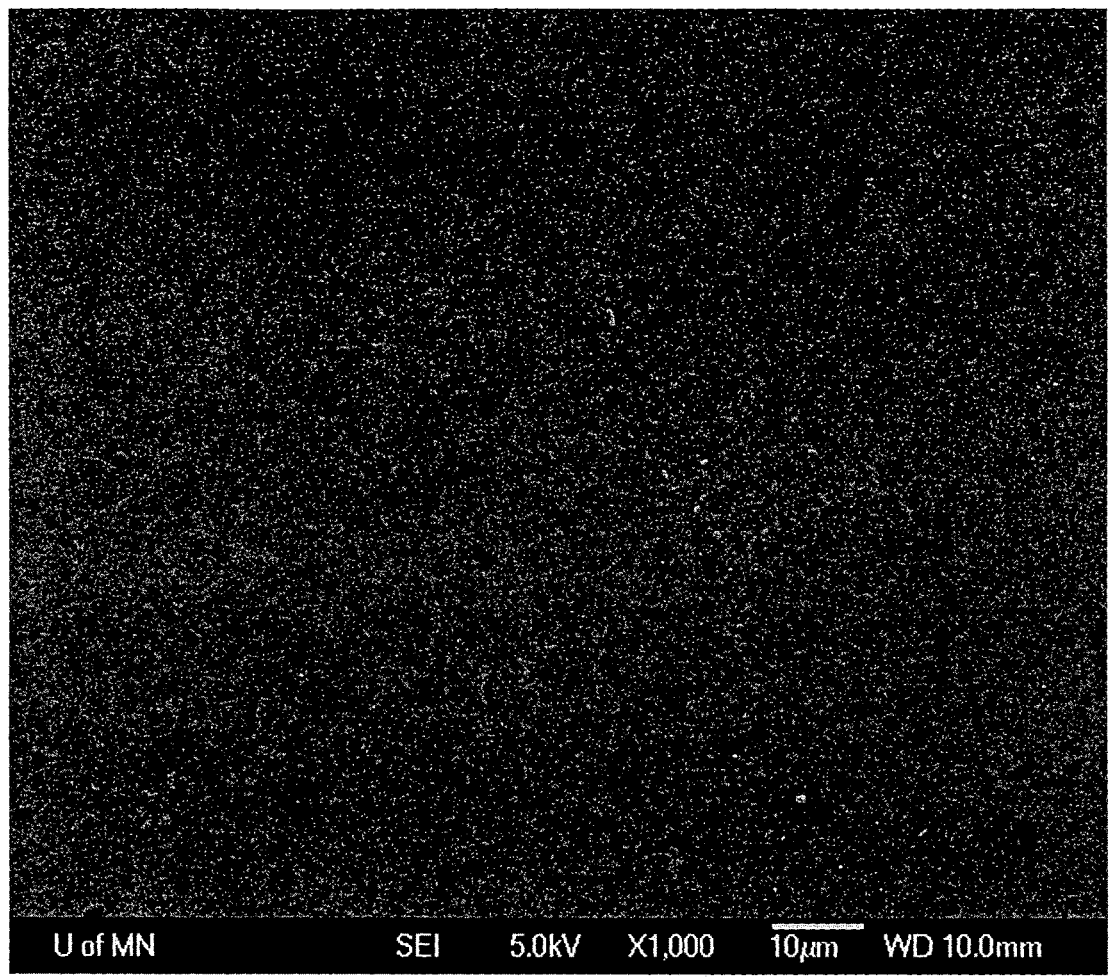
FIG. 2 is a magnified image of a clean pyrolytic carbon valve assembly.

A pyrolytic carbon aortic valve assembly manufactured by ATS Medical, Inc. of Plymouth, Minn. as Model #500FA-25 having a surface area of 12.42 cm$^2$ was cleaned by wiping with ethyl alcohol and subsequent air drying for ten minutes. The cleaned pyrolytic valve assembly was inspected under a scanning electron microscope at a magnification of 1000×. A photograph from such inspection is shown in FIG. 2.

Example I

Figure 3:
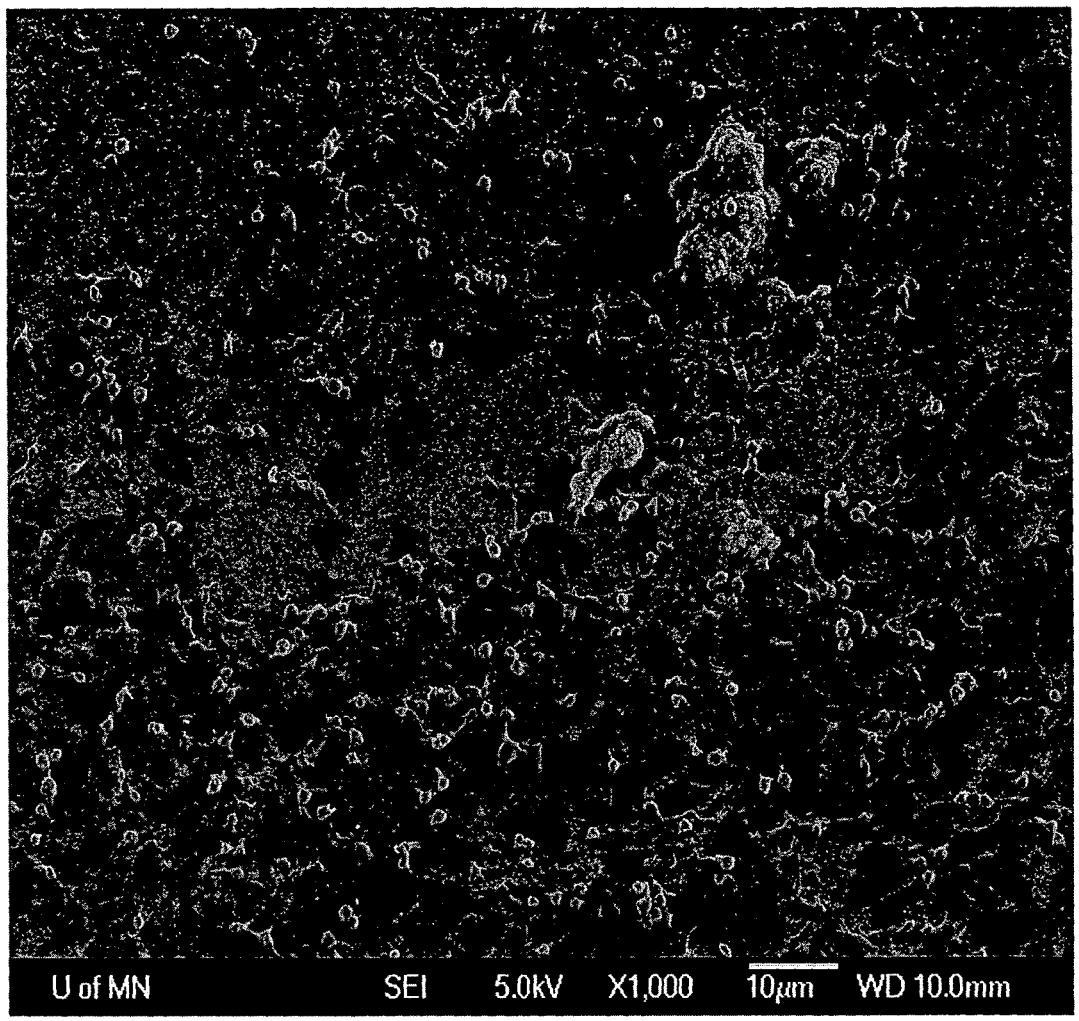
FIG. 3 is a magnified image of a pyrolytic carbon valve assembly subsequent to exposure to human blood.

A pyrolytic carbon aortic valve assembly similar to that utilized in the control was cleaned as described with reference to the control procedure. The pyrolytic carbon valve assembly was exposed to a first 200 ml aliquot of a human blood sample for 45 min. at 37° C. in a pulsatile blood perfusion system. The blood perfusion system was arranged with an approximate output of 5 L per min. The valve leaflets of the assembly were oriented in the blood perfusion system with their respective major planes disposed parallel to axial blood flow through the system. Subsequent to the exposure to the human blood, the pyrolytic carbon valve assembly was removed from the system, rinsed in saline, and inspected under scanning electron microscope at a magnification of 1,000×, with an image from such inspection being shown in FIG. 3. The image illustrates completely confluent blood platelet adhesion.

Example II

A pyrolytic carbon valve assembly similar to those utilized in the control and in Example I was cleaned through the protocol identified in the control. The cleaned pyrolytic carbon valve assembly was exposed to a second 200 mL aliquot of the human blood sample for 45 min. at 37° C. in a pulsatile blood perfusion system. The blood perfusion system was set up with an approximate output of 5 L per min. An electrical lead was electrically connected to the valve assembly carrying a current of 3.0 mA to create electropositive current density of 0.24 mA/cm$^2$ at the valve assembly. The current was delivered as a pulsed square waveform having a 25 ms duration pulse at 20 Hz. The valve leaflets were axially oriented in the blood perfusion system, such that the major planes of the respective valve leaflets were parallel to the direction of blood flow.

Figure 4:
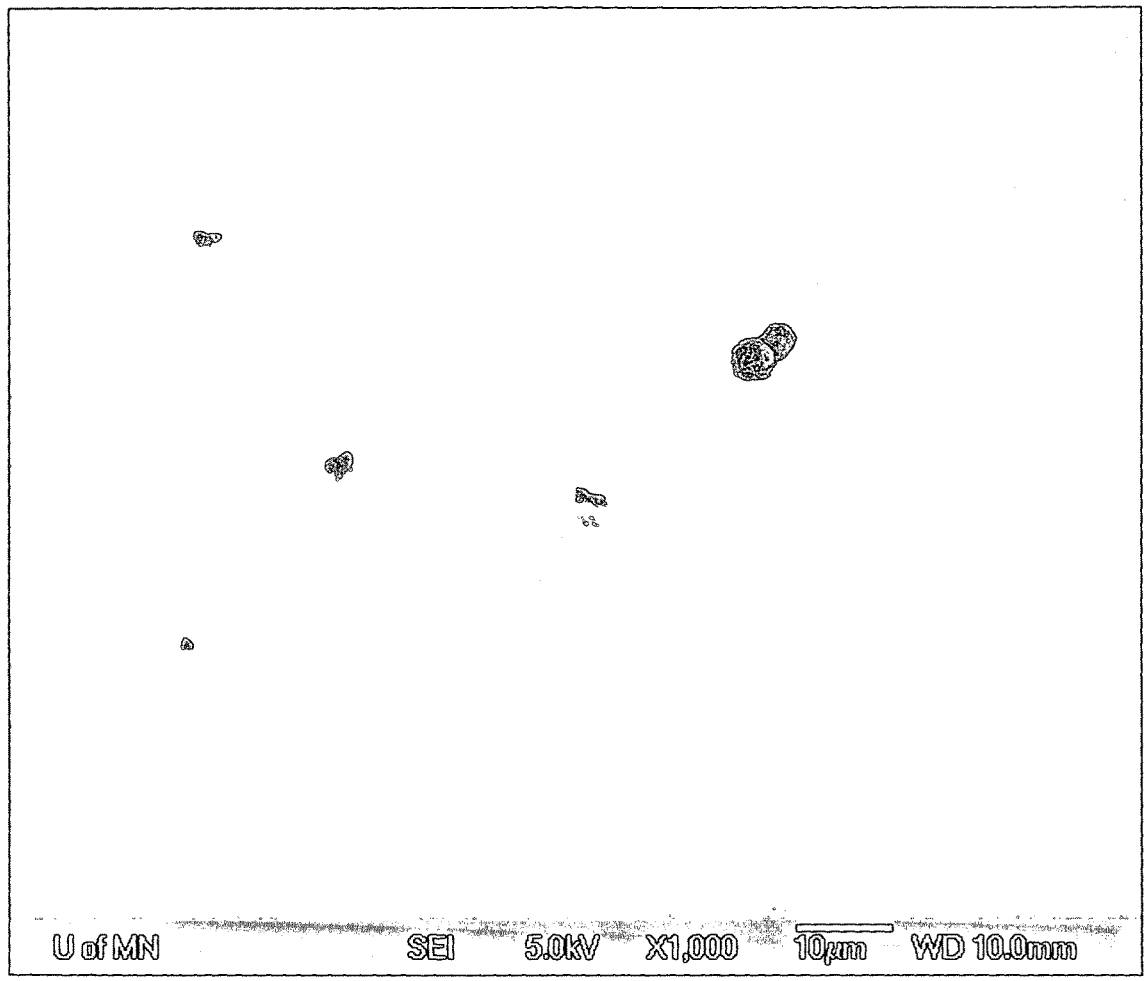
FIG. 4 is a magnified image of a pyrolytic carbon valve assembly subsequent to exposure to human blood while being supplied with electropositive current.

Upon completion of 45 min. of exposure to the blood perfusion system, the valve assembly was removed from the system, rinsed in saline, and examined under a scanning electron microscope at a magnification of 1000×. The image from such examination is shown in FIG. 4. As illustrated therein, very little platelet adhesion is observed. Such a result shows clear improvement over the blood platelet adhesion levels observed in Example I. Accordingly, the application of 0.24 mA/cm$^2$ of electropositive current density to the valve assembly significantly inhibited blood platelet adhesion thereon.

The invention has been described herein in considerable detail in order to comply with the patent statutes, and to provide those skilled in the art with the information needed to apply the novel principles and to construct and use embodiments of the invention as required. However, it is to be understood that the invention can be carried out by specifically different devices and that various modifications can be accomplished without departing from the scope of the invention itself.

What is claimed is:

1. A method for inhibiting thrombogenesis on a surface of a body in vivo, said method comprising:
    (a) providing an electrical energy source;
    (b) coupling said electrical energy source to said surface; and
    (c) delivering between about 0.1 and about 10 mA electropositive current from said electrical energy source to said surface to create an electropositive current density of between about 0.001 and about 1.0 mA/cm$^2$ on said surface.

2. A method as in claim 1 wherein said body is electrically conductive.

3. A method as in claim 1 wherein said body is an implanted medical device.

4. A method as in claim 3 wherein said implanted medical device is a medical heart valve.

5. A method as in claim 3 wherein said implanted medical device is a stent.

6. A method as in claim 1 wherein said electrical energy source is a pacemaker device.

7. A method as in claim 1 wherein said electrical energy source is coupled to said surface through one or more wires.

8. A method as in claim 1 wherein said current is delivered to said surface in pulsatile format.

9. A method as in claim 8 wherein said pulsatile current is in a wave form selected from the group consisting of sinusoidal, square, and triangular.

10. A method for inhibiting thrombogenesis on a surface of an electrically conductive body in vivo, said method comprising:
    electrically coupling said body to an electrical energy source, said electrical energy source delivering an electropositive current to said body to generate an electropositive current density of between about 0.001 and about 1.0 mA/cm$^2$ on said body.

11. A method as in claim 10 wherein said body is an implanted medical device.

12. A method for inhibiting blood component coagulation on a surface of an implanted medical device, said method comprising:
    electrically coupling said medical device to an electrical energy source such that said electrical energy source delivers electropositive current to said medical device to generate a sub-threshold current density on said medical device wherein said sub-threshold current density is between about 0.001 and 1.0 mA/cm$^2$.

13. A method as in claim 12 wherein said medical device is a mechanical heart valve.

14. A method for inhibiting blood platelet adhesion to a surface in vivo, said method comprising:
    applying electrical energy to said surface, said electrical energy being derived from an electropositive current creating a current density of between about 0.001 and about 1.0 mA/cm$^2$ on said surface.

15. A method as in claim 14 wherein said surface is located on an implanted medical device.

16. A method as in claim 15 wherein said implanted medical device is a mechanical heart valve.

17. A method as in claim 15 wherein said implanted medical device is a stent.

18. A method as in claim 14 wherein said surface is electrically conductive.

19. A method as in claim 14 wherein said electrical energy is delivered from an implanted energy source.

20. A method as in claim 19 wherein said electrical energy source is a pacemaker device.

21. A method as in claim 19 wherein said electrical energy source is electrically coupled to said surface through one or more wires.

22. A method as in claim 14 wherein said current is in pulsatile format.

23. A method as in claim 22 wherein said pulsatile current is in a wave form selected from the group consisting of sinusoidal, square, and triangular.

24. A system for inhibiting thrombogenesis on a surface in vivo, said system comprising:
an electrical energy source electrically coupled to said surface, said electrical energy source providing electropositive current density of between about 0.001 and about 1.0 mA/cm$^2$ on said surface.

25. A system as in claim 24 wherein said surface is disposed on an implanted medical device.

26. A system as in claim 25 wherein said implanted medical device is a mechanical heart valve.

27. A system as in claim 25 wherein said implanted medical device is a stent.

28. A system as in claim 24 wherein said surface is electrically conductive.

29. A system as in claim 24 wherein said electrical energy source is electrically coupled to said surface through one or more wires.

30. A system as in claim 24 wherein said electrical energy source is a pacemaker device.

31. A system for inhibiting blood platelet adhesion on one or more surfaces of an implanted medical device, said system comprising:
an electrical current generating device electrically coupled to said implanted medical device through one or more wires, said electrical current generating device being disposed in the body of a patient and delivering an electropositive current to said one or more surfaces so as to create an electropositive current density of between about a 0.001 and about 1.0 m/cm$^2$ on said one or more surfaces.

32. A system as in claim 31 wherein said electrical current generating device is a pacemaker device.

* * * * *